United States Patent [19]

Atwal

[11] Patent Number: 4,769,371

[45] Date of Patent: Sep. 6, 1988

[54] DIHYDROPYRIMIDINE CARBOXYLIC ACID ESTERS

[75] Inventor: Karnail Atwal, Cranbury, N.J.

[73] Assignee: E. R. Squibb & Sons, Inc., Princeton, N.J.

[21] Appl. No.: 45,956

[22] Filed: May 1, 1987

[51] Int. Cl.⁴ ................ C07D 239/42; C07D 401/06; C07D 417/06; A61K 31/505

[52] U.S. Cl. ................ 514/275; 514/227.8; 514/232.2; 514/235.8; 514/212; 544/58.5; 544/58.4; 544/82; 544/122; 544/295; 544/332; 540/601

[58] Field of Search ............ 544/58.5, 58.4, 82, 544/122, 295, 332; 514/212, 222, 228, 232, 234, 236, 275; 540/601

[56] References Cited

PUBLICATIONS

Cho et al., "Synthesis of Novel Dihydropyrimidines and Tetrahydropyrimidines", J. Org. Chem., vol. 50, No. 22, (1985), pp. 4227-4230.

Primary Examiner—John M. Ford
Attorney, Agent, or Firm—Lawrence S. Levinson; Theodore R. Furman, Jr.

[57] ABSTRACT

Pyridine compounds of the formula

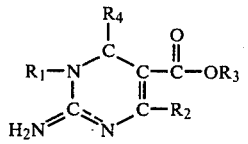

wherein $R_4$ is aryl or heterocyclo are disclosed. These compounds are useful as cardiovascular agents due to their calcium entry blocking vasodilator activity.

16 Claims, No Drawings

DIHYDROPYRIMIDINE CARBOXYLIC ACID ESTERS

FIELD OF THE INVENTION

The present invention relates to dihydropyrimidine carboxylic acid esters and more particularly concerns compositions and methods using such compounds as antihypertensive agents.

SUMMARY OF THE INVENTION

In accordance with the present invention novel pyrimidine derivatives, useful, for example, as antihypertensive agents, are disclosed. These compounds have the general formula

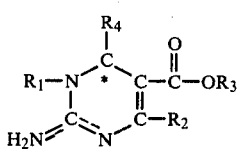   I wherein the compounds of formula I can exist as

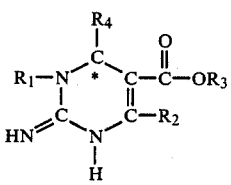   I' or

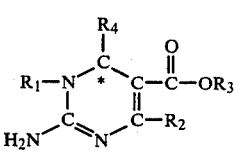   I'' or tautomeric mixtures thereof, including a pharmaceutically acceptable salt thereof, wherein $R_1$ is

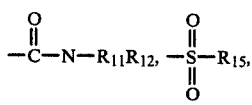

alkyl, cycloalkyl, alkenyl, alkynyl, aryl, —$(CH_2)_n$—$Y_1$, —$(CH_2)_q$—$Y_2$ or halo-substituted alkyl;

$R_2$ is hydrogen, lower alkyl, lower alkenyl, lower alkyl, cycloalkyl, aryl, —$A_1$-cycloalkyl, —$A_1$-aryl, —$A_1$-heterocyclo, —$A_1$—OH, —$A_1$—O—lower alkyl, —$A_1$—O—$(CH_2)_m$-aryl, —$A_1$—Sh, —$A_1$—S-lower alkyl, —$A_1$—S—$(CH_2)_m$-aryl,

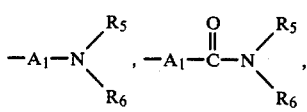

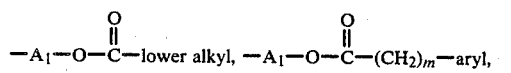

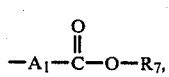

or halo substituted lower alkyl;

$R_3$ is hydrogen, lower alkyl, aryl, cycloalkyl, —$A_1$-aryl, —$A_1$-cycloalkyl, —$A_1$-heterocyclo, —$A_2$—OH, —$A_2$—O—lower alkyl, —$A_2$—O—$(CH_2)_m$-aryl, —$A_2$—SH, —$A_2$—S-lower alkyl, —$A_2$—S—$(CH_2)_m$-aryl,

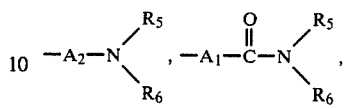

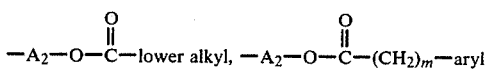

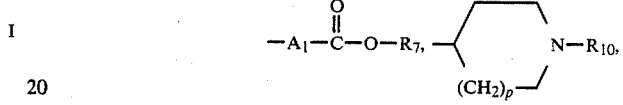

halo substituted lower alkyl, or a pharmaceutically acceptable salt forming ion;

$R_4$ is mono substituted phenyl wherein said substituent is selected from the group consisting of lower alkyl of 1 to 4 carbons, halo, $CF_3$, cyano and nitro, or disubstituted phenyl wherein said substituents are selected from the group consisting of methyl, halo, $CF_3$, and nitro;

$R_5$ and $R_6$ are independently selected from group consisting of hydrogen, lower alkyl, —$(CH_2)_m$-aryl,

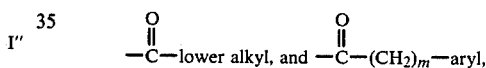

or $R_5$ and $R_6$ taken together with the N-atom to which they are attached complete a heterocyclic ring of the formula

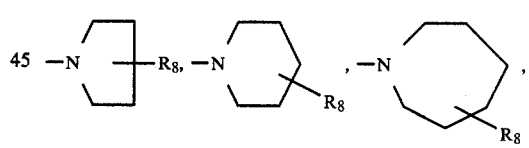

$R_7$ is hydrogen, lower alkyl, —$(CH_2)_m$-aryl or a pharmaceutically acceptable salt forming ion;

$R_8$ is hydrogen, lower alkyl of 1 to 4 carbons, lower alkoxy of 1 to 4 carbons, lower alkylthio of 1 to 4 carbons, halo, $CF_3$, nitro, or hydroxy;

$R_9$ is hydrogen, lower alkyl of 1 to 4 carbons,

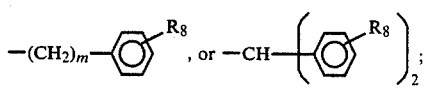

$R_{10}$ is lower alkyl of 1 to 4 carbons,

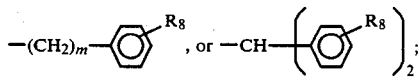

$R_{11}$ is alkyl, cycloalkyl, aryl, or arylalkyl and $R_{12}$ is alkyl, cycloalkyl, heterocyclo, —$(CH_2)_n$-$Y_1$, —$(CH_2)_q$-$Y_2$ or halo substituted alkyl, or $R_{11}$ and $R_{12}$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azeipinyl substituted with alkyl, alkoxy, alkylthio, halo, trifluoromethyl or hydroxy;

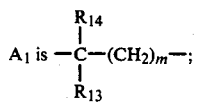

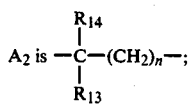

$R_{13}$ and $R_{14}$ are independently selected from the group consisting of hydrogen, lower alkyl of 1 to 4 carbons,

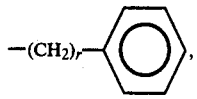

and —$(CH_2)_r$-cycloalkyl;

$R_{15}$ is alkyl, cylcoalkyl, alkenyl, alkynyl, aryl, —$(CH_2)_n$—$Y_1$, —$(CH_2)_q$—$Y_2$ or halo substituted alkyl;

$Y_1$ is cycloalkyl, aryl, heterocyclo, carbamoyl,

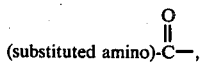

carboxyl, alkoxycarbonyl,

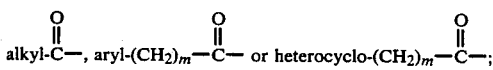

$Y_2$ is hydroxyl, alkoxy, aryl-$(CH_2)_m$—O—, mercapro, alkylthio, aryl-$(CH_2)_m$—S—,

amino, or substituted amino;
m is zero or an integer from 1 to 6;
n is an integer from 1 to 6;
p is zero, one or two;
q is an integer from 2 to 6; and,
r is zero or an integer from 1 to 3.

This invention is also directed to the novel pyrimidine compounds of formula I wherein $R_4$ is mono substituted phenyl wherein said substituent is selected from lower alkyl 1 to 4 carbons, halo, $CF_3$, and nitro, distributed phenyl wherein said substituents are selected from methyl, halo, $CF_3$, and nitro or heterocyclo.

DETAILED DESCRIPTION OF THE INVENTION

This invention in its broadest aspects relates to the pyrimidine compounds of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 3 to 7 carbon atoms with cyclopentyl and cyclohexyl being most preferred.

The term halo refers to chloro, bromo and fluoro.

The term halo substituted lower alkyl refers to such lower alkyl groups described above in which one or more lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, $CF_3$, NCS, $OCHF_2$,

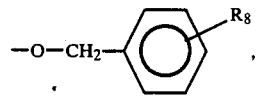

—$CH_2$-cycloalkyl,

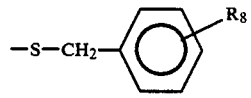

or —S—$CH_2$-cycloalkyl, and di-substituted phenyl.

The term heterocyclo refers to fully saturated or unsaturated monocyclic rings of 5 or 6 atoms containing one to four N atoms, or one O atom and up to two N atoms, or one S atom and up to two N atoms. The monocyclic ring is attached by way of an available carbon atom. Preferred monocyclic heterocyclo groups include 2- and 3-thienyl, 2- and 3-furyl, 2-, 3- and 4-pyridinyl. The term heterocyclo also includes 2-, 3-, or 4-pyridinyl rings having a substituent on one available carbon selected from lower alkyl of 1 to 4 carbons, lower alkylthio of 1 to 4 carbons, and lower alkoxy of 1 to 4 carbons, especially 2-methylthio-3-pyridinyl.

The compounds of formula I wherein $R_1$ is

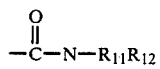

can be prepared by reacting an aldehyde of the formula $$R_4-CHO \qquad II$$

with a compound of the formula

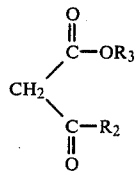

to produce a keto ester of the formula

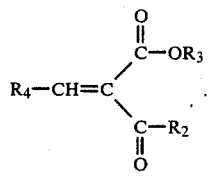

The compound of formula IV is treated with a pseudourea of the formula

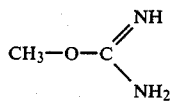

especially the hydrogen sulfate salt thereof, in the presence of sodium acetate or sodium bicarbonate to give the methoxy pyrimidine of the formula

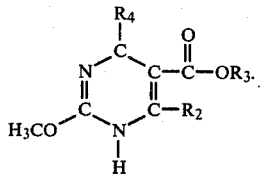

Compound VI can be treated with phosgene in the presence of pyridine and dichloromethane and is thereafter reacted with a compound of the formula $$NH-R_{11}R_{12} \qquad VII$$

to provide a compound of the formula

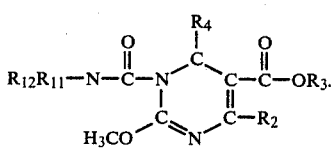

Compound VIII in the presence of an organic solvent, such as ethanol, is treated with ammonia to provide the compounds of formula I
(particularly of formula I″) wherein $R_1$ is

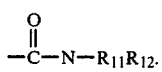

To prepare compounds of formula I where $R_1$ is

the compound of formula VI is treated with a sulfonyl chloride of the formula

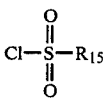

in the presence of pyridine to provide a compound of the formula

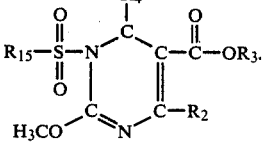

Compound X can thereafter be treated with ammonia in the presence of an organic solvent to provide the compounds of formula I (particularly of formula I″) wherein $R_1$ is

The compounds of the present invention wherein $R_1$ is other than

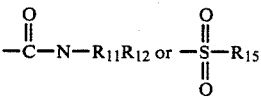

can be prepared in a similar manner. For example, the compounds of formula I where $R_1$ is alkyl, can be prepared by reacting the compounds of formula VI with an alkylating agent such as $$R_1\text{-halogen} \qquad XI$$

in the presence of an inorganic base to provide compounds of the formula

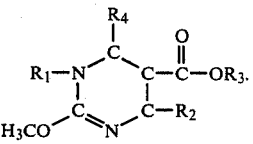

Compounds of formula XII can thereafter be treated with ammonia in the presence of an organic solvent to provide compounds of formula I (particularly of formula I') wherein $R_1$ is alkyl.

The compounds of formula I contain an asymmetric center within the pyrimidine ring as represented by the *. Thus, the compounds of formula I can exist in stereoisomeric forms or mixtures thereof. The above-described processes can utilize racemates, enantiomers or diastereomers as starting materials. When diastereomeric products are prepared, they can be separated by conventional chromatographic or fractional crystallization methods.

If any of $R_1$, $R_2$, $R_3$, $R_4$ and $R_{15}$ in the above are aryl, $-A_1$-aryl, or terminate in $-(CH_2)_m$-aryl wherein aryl is phenyl, 1-naphthyl, or 2-naphthyl substituted with one or more hydroxy or amino groups, heterocyclo, $-A_1$-heterocyclo or $-A_2$-heterocyclo wherein the heterocyclo ring contains an NH such as imidazolyl, or a substituted alkyl such as $-A_2-OH$, $-A_2-NH_2$, $-A_2-SH$, or

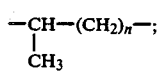

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred are those compounds of formula I wherein $R_1$ is

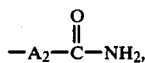

alkyl, alkenyl and $-(CH_2)_n-Y_1$;

$R_2$ is straight or branched chain lower alkyl of 1 to 5 carbons;

$R_3$ is straight or branched chain lower alkyl of 1 to 5 carbons, benzyl

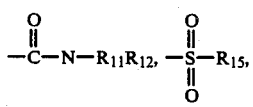

$R_4$ is mono-substituted phenyl wherein said substituent is selected from lower alkyl of 1 to 4 carbons, halo, $CF_3$, and nitro, or disubstituted phenyl wherein said substituents are selected from methyl, halo, $CF_3$ and nitro, 2-, 3-, or 4-pyridinyl, 2-methylthio-3-pyridinyl, or 2, 1, 3-benzoxadiazolyl;

$A_2$ is $-CH_2-(CH_2)_n-$ or

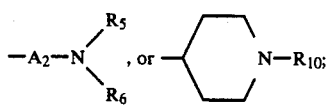

$R_5$ and $R_6$ are independently selected from hydrogen, straight or branched chain lower alkyl of 1 to 5 carbons, benzyl and $-(CH_2)_m$-aryl, or $R_5$ and $R_6$ taken together with the N atom to which they are attached completed a heterocyclic ring of the formula

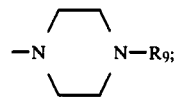

$R_9$ is methyl, benzyl or diphenylmethyl;
$R_{10}$ is benzyl or diphenylmethyl;
$Y_2$ is cycloalkyl, aryl or heterocyclo;
$R_{11}$ is alkyl;
$R_{12}$ is alkyl or $-(CH_2)_n-Y_1$;
$R_{15}$ is alkyl, aryl or $-(CH_2)_n-Y_1$; and,
n is zero, 1 or 2.

Most preferred compounds of the present invention are those compounds of formula I wherein $R_1$ is

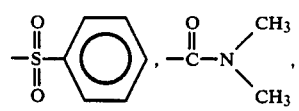

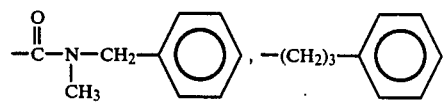

or $-CH_2-CH=CH_2$;
$R_2$ is methyl;
$R_3$ is ethyl, isopropyl, benzyl,

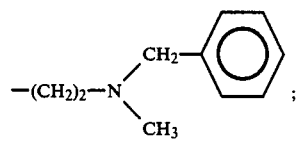

and
$R_4$ is 2-nitrophenyl, 3-nitrophenyl, 2-chlorophenyl, 3-chlorophenyl, 2-(trifluoromethyl)phenyl, 3-(trifluoromethyl)-phenyl, 2,3-dichlorophenyl, 2-chloro-3-nitrophenyl.

The compounds of formula I which contain an amino group form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_2$ or $R_3$ is

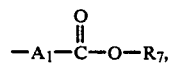

or in which $R_3$ is hydrogen, include carboxylic acid salts, i.e., $R_3$ or $R_7$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg per kilogram of body weight per day, preferably from about 1 to about 50 mg per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

HA421

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will be further described by reference to the following examples, however, it should not be limited by the details therein.

EXAMPLE 1

2-Amino-1,6-dihydro-4-methyl-6-(3-nitrophenyl)-1-(phenylsulfonyl)-5-pyrimidinecarboxylic acid, ethyl ester

A.

1,4-Dihydro-2-methoxy-6-methyl-4-(3-nitrophenyl)-5-pyrimidinecarboxylic acid, ethyl ester A reaction mixture containing 2-[(3-nitrophenyl)methylene]-3-oxobutanoic acid, ethyl ester (2.62 g, 10.0 mmole), 2-methylpseudourea sulfate (1.72 g, 10.0 mmole), and sodium acetate (1.8 g, 22.0 mmole) in tetrahydrofuran (10 ml) is heated under reflux for 4 hours. The reaction mixture is allowed to cool to room temperature, diluted with ethyl acetate, and filtered. The filtrate is washed with sodium bicarbonate and brine, and then dried over anhydrous magnesium sulfate. Evaporation of the solvent gives a yellow oil which is purified by flash chromatography (5% ethyl acetate in dichloromethane). The resulting foam is crystallized from isopropyl ether-hexanes to provide 1.53 g of 1,4-dihydro-2-methoxy-6-methyl-4-(3-nitrophenyl)-5-pyrimidinecarboxylic acid, ethyl ester as a colorless crystalline product; m.p. 103.5°–105°. TLC (silica gel; ethyl acetate:hexanes, 50:50) $R_f=0.31$.

Anal. calc'd for $C_{15}H_{17}N_3O_5$: C, 56.42: H, 5.37: N, 13.16; Found: C, 56.52; H, 5.35; N, 13.03.

B.

1,6-Dihydro-2-methoxy-4-methyl-6-(3-nitrophenyl)-1-(phenylsulfonyl)-5-pyrimidinecarboxylic acid, ethyl ester A solution of the title A compound (3.19 g, 10.0 mmol) and distilled triethylamine (4.18 ml, 30.0 mmol) in distilled dichloromethane (20 ml) in an ice bath under argon was treated dropwise via syringe with benzenesulfonyl chloride (1.53 ml, 12.0 mmol). The reaction was stirred at room temperature for 48 hours. It was then partitioned between ethyl acetate and water. The organic phase was washed with saturated sodium chloride and flash chromatograhed to give 2.94 g of the title B compound as a light brown oil.

C.

2-Amino-1,6-dihydro-4-methyl-6-(3-nitrophenyl)-1-(phenylsulfonyl)-5-pyrimidinecarboxylic acid, ethyl ester A solution of the sulfonamide of part B (1.45 g, 3.16 mmol) in distilled tetrahydrofuran (20 ml) in an ice bath was saturated with ammonia gas, capped and allowed to stand at room temperature overnight. The reaction mixture was re-saturated with ammonia gas (0° C.) and allowed to stand at room temperature overnight. The reaction was then evaporated, flash chromatographed, and crystallized from dichloromethane/isopropyl ether to give 415 mg of the title compound as colorless crystals; m.p. 200°–200° C.

Microanalysis for $C_{20}H_{20}N_4O_6S$: Calculated: C, 54.05; H, 4.54; N, 12.61; S, 7.21; Found: C, 54.19; H, 4.53; N, 12.73; S, 7.18.

EXAMPLE 2

1,2,3,6-Tetrahydro-2-imino-4-methyl-6-(3-nitrophenyl)-1-(2-propenyl)-5-pyrimidinecarboxylic acid, 1-methylethyl ester, monohydrochloride

A.

1,4-Dihydro-2-methoxy-6-methyl-4-(3-nitrophenyl)-5-pyrimidinecarboxylic acid, methylethyl ester The title A compound can be prepared by using the procedure of part A from Example 1, but starting with 2-[(3-nitrophenyl)methylene]-3-oxabutanoic acid, methylethyl ester.

B.

1,6-Dihydro-2-methoxy-4-methyl-6-(3-nitrophenyl)-1-(2-propenyl)-5-pyrimidinecarboxylic acid, 1-methylethyl ester The solution of the title A compound (4.0 g, 12.0 mmoles) in dry dimethylformamide (10 ml) was treated with finely ground potassium carbonate (6.6 g, 48.0 mmoles) and allyl bromide (1.7 ml, 20.0 mmoles). The resulting suspension was allowed to stir under argon at room temperature for 10 hours. The reaction was diluted with ethyl acetate, filtered and the filtrate was washed with water and brine. It was dried over anhydrous magnesium sulfate and evaporated to provide a yellow oil. Purification by flash chromatography (20% ethyl acetate in hexanes) yielded the title B compound (2.64 g) as yellow oil.

C.

1,2,3,6-Tetrahydro-2-imino-4-methyl-6-(3-nitrophenyl)-1-(2-propenyl)-5-pyrimidinecarboxylic acid, 1-methylethyl ester, monohydrochloride A reaction mixture containing the title B compound (1.06 g, 2.84 mmoles) and ammonium acetate (221 mg, 2.71 mmoles) in methanol (10 ml) was cooled in an ice bath and ammonia gas was slowly bubbled through it until saturation. The reaction was heated in a sealed tube at 90°–100° C. for 18 hours. It was cooled to ambient temperature and the solvent was evaporated. The residue was purified by flash chromatography (dichloromethane:methanol:acetic acid/18:1:1) to provide a colorless solid. It was dissolved in methylene chloride and treated with ether-hydrochloric acid (5 ml of 1N solution). The solvent and excess hydrochloric acid were removed and the residue was crystallized from acetonitrile-ether to yield 480 mg of the title compound as colorless solid, m.p. 208°–210° C. (darkens).

Microanalysis for $C_{18}H_{22}N_4O_4 \cdot HCl$: Calculated: C, 54.75; H, 5.87; N, 14.19; Cl, 8.98; Found: C, 54.38; H, 5.80; N, 14.00; Cl, 9.03.

EXAMPLE 3

1,2,3,6-Tetrahydro-2-imino-4-methyl-6-(3-nitrophenyl)-1-(3-phenylpropyl)-5-pyrimidinecarboxylic acid, 1-methylethyl ester, monohydrochloride

A.

1,6-Dihydro-2-methoxy-4-methyl-6-(3-nitrophenyl)-1-(3-phenylpropyl)-5-pyrimidinecarboxylic acid, 1-methylethyl ester A solution of the methoxypyrimidine from part A of Example 2 (4.0 g, 12 mmol) in dry dimethylformamide (10 ml) under argon was treated with finely ground potassium carbonate (4.97 g, 36.0 mmoles), 3-phenylpropyl bromide (2.19 ml, 14.4 mmoles) and catalytic amount of 18-crown-6. The resulting suspension was allowed to stir at room temperature for 72 hours. It was diluted with ether, filtered and the filtrate was washed with water and brine. After drying over anhydrous magnesium sulfate, the solvent was evaporated. The residue was purified by flash chromatography (15% ethyl acetate in hexanes) to provide the desired product (3.29 g) as yellow oil.

B.

1,2,3,6-Tetrahydro-2-imino-4-methyl-6-(3-nitrophenyl)-1-(3-phenylpropyl)-5-pyrimidinecarboxylic acid, 1-methylethyl ester, monohydrochloride The solution of the title A compound (1.30 g, 2.88 mmoles) in methanol (10 ml) was cooled to 0° C. and ammonia gas was slowly bubbled through the solution until near saturation. Ammonium acetate (221 mg, 2.70 mmoles) was added and the resulting reaction was heated at 90°–100° C. in a sealed tube for 16 hours. The solvent was evaporated and the residue was purified by flash chromatography (dichloromethane:methanol:acetic acid/18:1:1). The residue, after evaporation of the solvent, was taken up in methylene chloride and was treated with etherial hydrochloric acid (5 ml of 1N solution). The solvent was evaporated and the residue was crystallized from acetonitrileisopropryl ether to provide 610 mg of the title compound as a colorless solid, m.p. 162.5°–165° C.

Microanalysis for $C_{24}H_{28}N_4O_4 \cdot HCl$: Calculated: C, 60.95; H, 6.18; N, 11.85; Cl, 7.50; Found: C, 60.79; H, 6.12; N, 11.73; Cl, 7.68.

EXAMPLE 4

2-Amino-1-[(dimethylamino)carbonyl]-1,6-dihydro-4-methyl-6-(3-nitrophenyl)-5-pyrimidinecarboxylic acid, 1-methylethyl ester

A.

1,6-Dihydro-1-[(dimethylamino)carbonyl]-2-methoxy-4-methyl-6-(3-nitrophenyl)-5-pyrimidinecarboxylic acid, 1-methylethyl ester A solution of the title A compound from Example 2 (3.34 g, 10.0 mmol) and distilled triethyl amine (6.3 ml, 45 mmol) in dichloromethane (10 ml) in an ice bath under argon was treated dropwise via GT syringe with 1.3 M phosgene in benzene solution (9.2 ml, 12 mmol) over 3–5 minutes. After stirring at 0° C. for 1.5 hours, the reaction mixture was treated with 40 percent aqueous dimethyl amine (3.3 ml, 15 mmol), capped with a septum, and stirred at room temperature for 48 hours. The reaction was then evaporated and partitioned between ethyl acetate and water. The organic phase was washed with saturated sodium chloride, dried over potassium carbonate, and evaporated to give 4.75 grams of the title A compound as a brown oil.

B.

2-Amino-1-[(dimethylamino)carbonyl]-1,6-dihydro-4-methyl-6-(3-nitrophenyl)-5-pyrimidinecarboxylic acid, 1-methylethyl ester A solution of the compound of part A (2.48 g) in ethanol (50 ml) was cooled in an ice bath, saturated with ammonia gas and heated at 75° C. (oil bath) in a sealed tube for three days. The reaction mixture was evaporated, flash chromatographed (30–50% acetone in hexanes) and crystallized from dichloromethane/isopropyl ether to give 790 mg of the title B compound as yellow crystals, m.p. 202°–203° C.

Microanalysis for $C_{18}H_{23}N_5O_5$: Calculated: C, 55.52; H, 5.95; N, 17.98; Found: C, 55.35; H, 5.85; N, 17.80.

EXAMPLE 5

2-Amino-1,6-dihydro-4-methyl-1-[[methyl(phenylmethyl)amino]carbonyl]-6-(3-nitrophenyl)-5-pyrimidinecarboxylic acid, 1-methylethyl ester

A.

1,6-Dihydro-2-methoxy-4-methyl-1-[[methyl(phenylmethyl)amino]carbonyl]-6-(3-nitrophenyl)-5-pyrimidinecarboxylic acid, 1-methylethyl ester A solution of the title A compound from Example 2 (3.34 g, 10 mmol) and dry triethylamine (6.3 ml, 45 mmol) in dichloromethane (10 ml) in an ice bath under argon was treated dropwise via GT syringe with 1.3 M phosgene in benzene solution (9.2 ml, 12 mmol). The resulting mixture was stirred in the bath for 20 hours. After cooling to 0° C. the mixture was treated with benzylmethylamine (1.95 ml, 15 mmol) and stirred at room temperature overnight. The reaction was then diluted with dichloromethane and washed with water, saturated sodium chloride, dried over potassium carbonate and evaporated. The residue was passed through a short column of silica, eluting with 20 percent acetone/hexanes. The product fractions were combined, evaporated and triturated with isopropyl ether to give 4.11 g of the title A compound as white crystals, m.p. 145°-146° C. (softens 140° C.).

B.
2-Amino-1,6-dihydro-4-methyl-1-[[methyl(phenylmethyl)amino]carbonyl]-6-(3-nitrophenyl)-5-pyrimidinecarboxylic acid, 1-methylethyl ester A suspension of the title A compound (2.30 g, 4.98 mmol) in isopropanol (50 ml) was cooled in an ice bath and saturated with ammonia gas. The reaction mixture was heated at 50° C. in a sealed tube for 10 hours. Most of the starting material precipitated out so the mixture was transferred to a pressure vessel. After diluting with isopropanol (25 ml) and tetrahydrofuran (75 ml), the resulting solution was resaturated with ammonia gas, treated with glacial acetic acid (3 drops), stoppered and heated at 50° C. overnight. The solution was cooled to 0° C., resaturated with ammonia gas and heated at 70° C. overnight. The solvent was evaporated and the residue was purified by flash chromatography. Crystallization from dichloromethane/isopropyl ether gave 1.083 g of the title compound as a light yellow solid, m.p. 129°-130° C.

Microanalysis for $C_{24}H_{27}N_5O_5$: Calculated: C, 61.92; H, 5.85; N, 15.04; Found: C, 61.72; H, 5.78; N, 14.78.

EXAMPLES 6-31

Following the methods and procedures outlined above and in Examples 1-5, the following additional compounds of formula I within the scope of the present invention can be prepared.

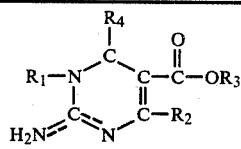

| Ex. No. | $R_1$ | $R_2$ | $R_3$ | $R_4$ |
|---|---|---|---|---|
| 6 | -S(O)₂-phenyl | -CH₃ | -(CH₂)₂-N(CH₃)-CH₂-phenyl | 2-nitrophenyl |
| 7 | -C(O)-N(CH₃)₂ | -CH₃ | -CH₂-phenyl | 3-chlorophenyl |
| 8 | -C(O)-N(CH₃)-CH₂-phenyl | -C₂H₅ | -CH₂-cyclohexyl | pyridyl |
| 9 | -(CH₂)₃-phenyl | -CH₃ | -(CH₂)₂-pyridyl | 2-nitrophenyl |
| 10 | -CH₂-CH=CH₂ | -CH₃ | -(CH₂)₂-O-CH₃ | 4-(trifluoromethyl)phenyl |
| 11 | -S(O)₂-(CH₂)₂-phenyl | -CH₃ | -(CH₂)₂-O-phenyl | 2-chloro-3-nitrophenyl |
| 12 | -S(O)₂-(CH₂)₃CH₃ | -CH₃ | -CH₃ | 2,3-dichlorophenyl |

-continued

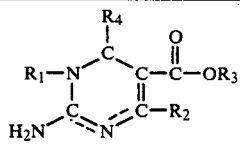

| Ex. No. | R₁ | R₂ | R₃ | R₄ |
|---|---|---|---|---|
| 13 | −C(O)−N(CH₃)−(CH₂)₂−C₆H₅ | −CH₂−C₆H₅ | −CH(CH₃)₂ | 2-NO₂-C₆H₄ |
| 14 | −C(O)−N(C₂H₅)(CH₃) | −CH₃ | −CH(CH₃)₂ | 2,3-F₂-C₆H₃ |
| 15 | −C(O)−N(piperidinyl, 5-ring: pyrrolidinyl) | −CH₃ | −CH(CH₃)₂ | 4-pyridyl |
| 16 | −C(O)−N(piperidinyl) | −CH₃ | −(CH₂)₂−O−C(O)−C₂H₅ | 2-NO₂-C₆H₄ |
| 17 | −(CH₂)₂−cyclohexyl | −CH₃ | −(CH₂)₂−O−C(O)−CH₂ | 4-CF₃-C₆H₄ |
| 18 | −(CH₂)₂−(3-pyridyl) | −CH₃ | −(CH₂)₂−C(O)−O−C₂H₅ | 2,3-Cl₂-C₆H₃ |
| 19 | −CH₂−CH₂−CH=CH₂ | −CH₃ | −C₂H₅ | 2-Br-C₆H₄ |
| 20 | −S(O)₂−C₆H₅ | −CH₃ | −C₂H₅ | 3-Br-C₆H₄ |
| 21 | −C(O)−N(CH₃)₂ | −CH₃ | −CH₃ | 2-CN-C₆H₄ |
| 22 | −C(O)−N(C₂H₅)(CH₂−C₆H₅) | −CH₃ | −C₂H₅ | 3-Br-C₆H₄ |

-continued

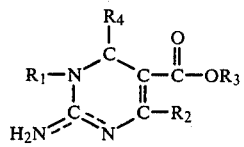

| Ex. No. | R₁ | R₂ | R₃ | R₄ |
|---|---|---|---|---|
| 23 | —(CH₂)₂—C₆H₅ | —CH₃ | —CH—(CH₃)₂ | 3-(CF₃)C₆H₄— |
| 24 | —CH₂—CH=CH₂ | —CH₃ | —CH—(CH₃)₂ | 2-Cl-3-NO₂-C₆H₃— |
| 25 | —(CH₂)₂-(3-pyrrolidinyl) | —CH₃ | —(CH₂)₂—O—CH₂—C₆H₅ | 2-Cl-C₆H₄— |
| 26 | —C(O)—N(C₃H₇)(C₂H₅) | —CH₃ | —CH(CH₃)—CH₂—N(CH₃)—CH₂—C₆H₅ | 3-NO₂-C₆H₄— |
| 27 | —S(O)₂—(CH₂)₂-(4-piperidinyl) | —CH₃ | —C₂H₅ | 2,6-Cl₂-C₆H₃— |
| 28 | —C₃H₇ | —CH₃ | —C₂H₅ | 2,3-Cl₂-C₆H₃— |
| 29 | —C₂H₅ | —CH₃ | —C₂H₅ | 2-CH₃-C₆H₄— |
| 30 | —(CH₂)₃—N(thiomorpholinyl) | —CH₃ | —CH₂—CH—(CH₃)₂ | 2-OCHF₂-C₆H₄— |
| 31 | —C(O)—N(CH₃)₂ | —CH₃ | —C₂H₅ | 2-Br-3-pyridyl |

What is claimed is:

1. A compound having the formula

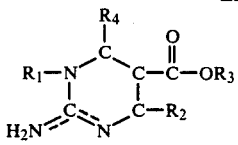

wherein the compounds of formula I can exist as

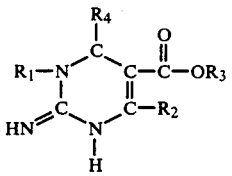

or

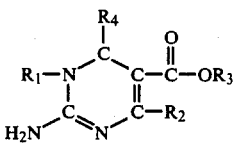

or tautomeric mixtures thereof, including a pharmaceutically acceptable salt thereof, wherein R₁ is

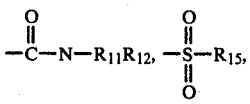

alkyl [of 2 or more carbon atoms] of 2 to 8 carbon atoms, cycloalkyl, lower alkenyl, lower alkynyl, aryl, $-(CH_2)_n-Y_1$, $-(CH_2)_q-Y_2$ or halo-substituted lower alkyl;

R₂ is hydrogen, lower alkyl, lower alkenyl, lower alkyl, cycloalkyl, aryl, $-A_1$-cycloalkyl, $-A_1$-aryl, $-A_1-OH$, $-A_1-O$-lower alkyl, $-A_1-O-(CH_2)_m$-aryl, $-A_1-SH$, $-A_1-S$-lower alkyl, $-A_1-S-(CH_2)_m$-aryl,

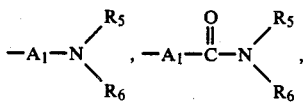

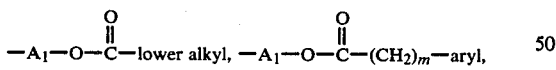

halo substituted lower alkyl;

R₃ is hydrogen, lower alkyl, aryl, cycloalkyl, $-A_1$-aryl, $-A_1$-cycloalkyl, $-A_2-OH$, $-A_2-O$-lower alkyl, $-A_2-O-(CH_2)_m$-aryl, $-A_2-SH$, $-A_2-S$-lower alkyl, $-A_2-S-(CH_2)_m$-aryl,

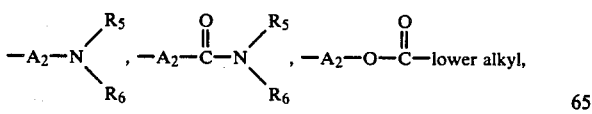

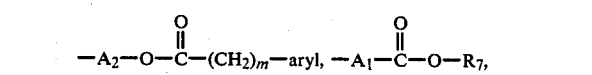

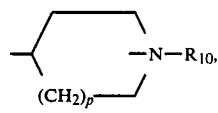

halo substituted lower alkyl, or a pharmaceutically acceptable salt forming ion;

R₄ is mono substituted phenyl wherein said substituent is selected from the group consisting of lower alkyl of 1 to 4 carbons, halo, CF₃, cyano and nitro, or disubstituted phenyl wherein said substituents are selected from the group consisting of methyl, halo, CF₃, and nitro;

R₅ and R₆ are independently selected from the group consisting of hydrogen, lower alkyl, $-(CH_2)_m$-aryl, $$-\overset{O}{\underset{\|}{C}}-\text{lower alkyl, and } -\overset{O}{\underset{\|}{C}}-(CH_2)_m-\text{aryl,}$$

or R₅ and R₆ taken together with the N-atom to which they are attached complete a heterocyclic ring of the formula

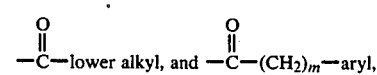

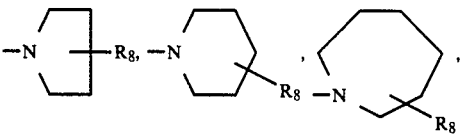

R₇ is hydrogen, lower alkyl, $-(CH_2)_m$-aryl or a pharmaceutically acceptable salt forming ion;

R₈ is hydrogen, lower alkyl of 1 to 4 carbons, lower alkoxy of 1 to 4 carbons, lower alkylthio of 1 to 4 carbons, halo, CF₃, nitro or hydroxy;

R₉ is hydrogen, lower alkyl of 1 to 4 carbons,

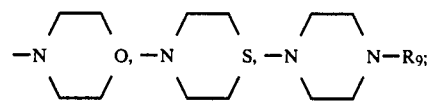

R₁₀ is lower alkyl of 1 to 4 carbons,

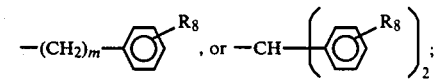

R₁₁ is lower alkyl, cycloalkyl, aryl, or aryl-lower alkyl and R₁₂ is lower alkyl, cycloalkyl, $-(CH_2)_n-Y_1$, $-(CH_2)_q-Y_2$ or halo substituted lower alkyl or R₁₁ and R₁₂ taken together with the nitrogen atom to which they ar eattached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diaralkyl-1-piperazinyl or 1-pyrrolidinyl, 1-piperidinyl, or 1-azeipinyl substituted with lower alkyl, lower alkoxy, lower alkylthio, halo trifluoromethyl or hydroxy;

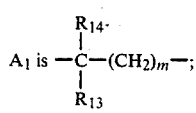

$A_1$ is

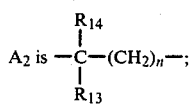

$A_2$ is $R_{13}$ and $R_{14}$ are independently selected from the group consisting of hydrogen, lower alkyl of 1 to 4 carbons,

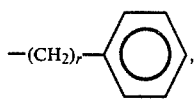

and —(CH$_2$)$_r$-cycloalkyl;
$R_{15}$ is lower alkyl, cycloalkyl, lower alkenyl, lower alkynyl, aryl, —(CH$_2$)$_n$—Y$_1$, —(CH$_2$)$_q$—Y$_2$ or halo substituted lower alkyl;
Y$_1$ is cycloalkyl, aryl, carbamoyl,

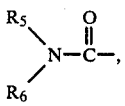

carboxyl, lower alkoxycarbonyl,

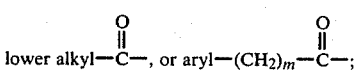

Y$_2$ is hydroxyl, lower alkoxy, aryl-(CH$_2$)$_m$—O, mercapto, lower alkylthio, aryl-(CH$_2$)$_m$—S—,

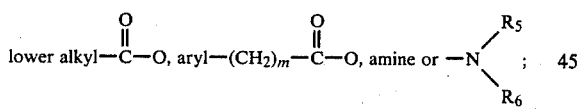

m is zero or an integer from 1 to 6;
n is an integer from 1 to 6;
p is zero, one or two;
q is an integer from 2 to 6; and,
r is zero or an integer from 1 to 3;
wherein the term cycloalkyl refers to saturated rings of 3 to 7 carbon atoms; and,
the term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)$_2$, wherein alkyl is of 1 to 4 carbons, CF$_3$, NCS, OCHF$_2$,

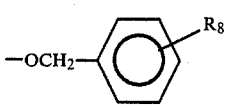

—CH$_2$-cycloalkyl,

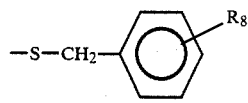

or —S—CH$_2$-cycloalkyl, and di-substituted phenyl;
wherein the substituents are selected from the group consisting of methyl, halo, CF$_3$ and nitro;
the term lower alkyl refers to straight or branched chain hydrocarbon radicals of 1 to 8 carbon atoms;
the term lower alkenyl refers to straight or branched chain hydrocarbon radicals of 2 to 8 carbon atoms having one double bond; and,
the term lower alkynyl refers to straight or branched chain hydrocarbon radicals of 2 to 8 carbon atoms having one triple bond.

2. The compound claim 1 wherein wherein $R_1$ is

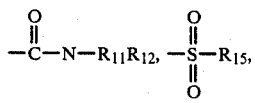

alkyl of 2 to 8 carbon atoms, alkenyl and —(CH$_2$)$_n$—Y$_1$;
$R_2$ is straight or branched chain lower alkyl of 1 to 5 carbons;
$R_3$ is straight or branched chain lower alkyl of 1 to 5 carbons, benzyl

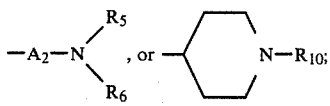

$R_4$ is mono-substituted phenyl wherein said substituent is selected from lower alkyl of 1 to 4 carbons, halo, CF$_3$, and nitro, or disubstituted phenyl wherein said substituents are selected from methyl, halo, CF$_3$ and nitro, 2-, 3-, or 4-pyridinyl, 2-methylthio-3-pyridinyl, or 2, 1, 3-benzooxadiazolyl;
$A_2$ is —CH$_2$—(CH$_2$)$_n$— or

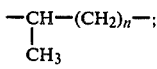

$R_5$ and $R_6$ are independently selected from hydrogen, straight or branched chaon lower alkyl of 1 to 5 carbons, benzyl and —(CH$_2$)$_m$-aryl, or $R_5$ and $R_6$ taken together with the N atom to which they are attached complete a heterocyclic ring of the formula

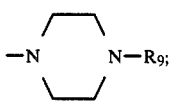

$R_9$ is methyl, benzyl or diphenylmethyl;
$R_{10}$ is benzyl or diphenylmethyl;
$Y_2$ is cycloalkyl, aryl or heterocyclo;

$R_{11}$ is alkyl;
$R_{12}$ is alkyl or $-(CH_2)_n-Y_1$;
$R_{15}$ is alkyl, aryl or $-(CH_2)_n-Y_1$; and,
n is zero, 1 or 2.

3. The compound of claim 2 wherein invention are those compounds of formula I wherein
$R_1$ is

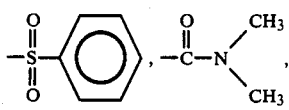, 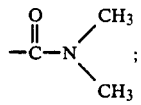

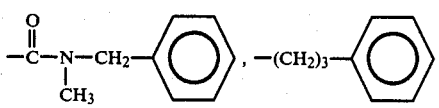, 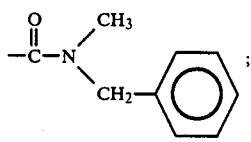

or $-CH_2-CH=CH_2$;
$R_2$ is methyl;
$R_3$ is ethyl, isopropyl, benzyl,

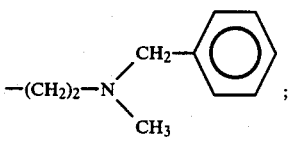

and
$R_4$ is 2-nitrophenyl, 3-nitrophenyl, 2-chlorophenyl, 3-chlorophenyl, 2-(trifluoromethyl)phenyl, 3-(trifluoromethyl)-phenyl, 2,3-dichlorophenyl, 2-chloro-3-nitrophenyl, or 4-(2,1,3-benzoxadiazol)-yl.

4. A compound of claim 1 wherein
$R_1$ is

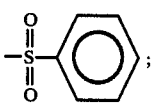;

$R_2$ is methyl;
$R_3$ is $C_2H_5$; and,
$R_4$ is 3-nitrophenyl.

5. A compound of claim 1 wherein
$R_1$ is $-CH_2-CH=CH_2$;
$R_2$ is methyl;
$R_3$ is isopropyl; and,
$R_4$ is 3-nitrophenyl.

6. A compound of claim 1 wherein
$R_1$ is

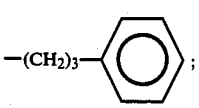;

$R_2$ is methyl;
$R_3$ is isopropyl; and,
$R_4$ is 3-nitrophenyl.

7. A compound of claim 1 wherein
$R_1$ is $R_2$ is methyl;
$R_3$ is isopropyl; and,
$R_4$ is 3-nitrophenyl.

8. A compound of claim 1 wherein
$R_1$ is $R_2$ is methyl;
$R_3$ is isopropyl; and,
$R_4$ is 3-nitrophenyl.

9. The compound of claim 1 having the name 2-amino-1,6-dihydro-4-methyl-6-(3-nitrophenyl)-1-(phenylsulfonyl)-5-pyrimidinecarboxylic acid, ethyl ester.

10. The compound of claim 1 having the name 1,2,3,6-tetrahydro-2-imino-4-methyl-6-(3-nitrophenyl)-1-(2-propenyl)-5-pyrimidinecarboxylic acid, 1-methylethyl ester, monohydrochloride.

11. The compound of claim 1 having the name 1,2,3,6-tetrahydro-2-imino-4-methyl-6-(3-nitrophenyl)-1-(3-phenylpropyl)-5-pyrimidinecarboxylic acid, 1-methylethyl ester, monohydrochloride.

12. The compound of claim 1 having the name 2-amino-1-[(dimethylamino)carbonyl]-1,6-dihydro-4-methyl-6-(3-nitrophenyl)-5-pyrimidinecarboxylic acid, 1-methylethyl ester.

13. The compound of claim 1 having the name 2-amino-1,6-dihydro-4-methyl-1-[[methyl(phenylmethyl)amino]carbonyl]-6-(3-nitrophenyl)-5-pyrimidinecarboxylic acid, 1-methylethyl ester.

14. A composition useful in reducing blood pressure in a mammal comprising a pharmaceutically acceptable carrier and an anti-hypertensively effective amount of a compound or pharmaceutically acceptable salt thereof of the formula

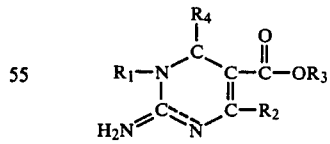

wherein $R_1$, $R_2$ and $R_3$ are as defined in claim 1 and $R_4$ is aryl;
wherein the term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, $CF_3$, NCS, $OCHF_2$,

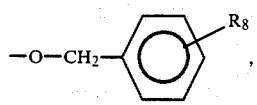

—CH$_2$-cycloalkyl,

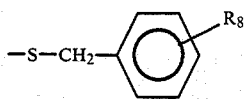

or —S—CH$_2$-cycloalkyl, and di-substituted phenyl;

wherein the substituents are selected from the group consisting of methyl, halo, CF$_3$ and nitro.

15. The composition of claim 11 wherein R$_4$ is mono substituted phenyl wherein said substituent is selected from the group consisting of lower alkyl of 1 to 4 carbons, lower alkoxy of 1 to 4 carbons, lower alkylthio of 1 to 4 carbons, halo, CF$_3$, cyano, nitro, benzyloxy, and —OCHF$_2$, disubstituted phenyl wherein said substituents are selected from the group consisting of methyl, methoxy, methylthio, halo, CF$_3$, and nitro.

16. The method of reducing blood pressure in a mammal comprising administering an effective amount of the composition of claim 11.

* * * * *

UNITED STATES PATENT AND TRADEMARK OFFICE
CERTIFICATE OF CORRECTION

PATENT NO. : 4,769,371
DATED : September 6, 1988
INVENTOR(S) : Karnail Atwal

It is certified that error appears in the above-identified patent and that said Letters Patent is hereby corrected as shown below:

Column 1, line 54, "$A_1$-Sh," should be --$A_1$-SH,--;

Column 2, line 31, insert --the-- after "from";

Column 3, line 52, "mercapro" should be --mercapto--;

Column 3, line 68 to Column 4, line 1, "distributed" should be --disubstituted--;

Column 9, line 21, delete "HA421";

Column 10, line 35, "200°-200°C." should be --200°-201°C.--;

Column 11, line 21, "$O_4$.HCl:" should be --$O_4 \cdot$HCl:--;

Column 12, line 1, "$O_4$.HCl:" should be --$O_4 \cdot$HCl:--;

Columns 15 and 16, the structure appearing between the top of both columns should be:

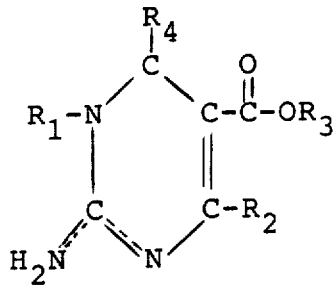

Column 19, line 34, delete "[of 2 or more carbon atoms]";

Column 19, line 56, insert --or-- before "halo";

UNITED STATES PATENT AND TRADEMARK OFFICE
CERTIFICATE OF CORRECTION

PATENT NO. : 4,769,371

DATED : September 6, 1988

INVENTOR(S) : Karnail Atwal

It is certified that error appears in the above-identified patent and that said Letters Patent is hereby corrected as shown below:

Column 20, line 63, "ar eattached" should be --are attached--;

Column 21, lines 1 and 2, "orhydroxy;" should be --or hydroxy;--;

Column 22, line 46, "3-benzooxadiazolyl;" should be --3-benzoxadiazolyl;--;

Column 22, line 55, "chaon" should be --chain--;

UNITED STATES PATENT AND TRADEMARK OFFICE
CERTIFICATE OF CORRECTION

PATENT NO. : 4,769,371

DATED : September 6, 1988

INVENTOR(S) : Karnail Atwal

It is certified that error appears in the above-identified patent and that said Letters Patent is hereby corrected as shown below:

Column 24, the formula between lines 50 and 60 should be:

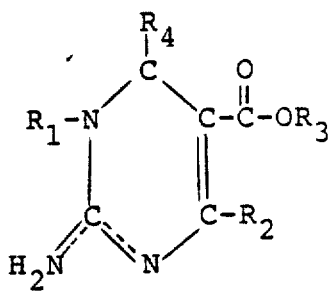

Signed and Sealed this

Twenty-fourth Day of January, 1989

Attest:

DONALD J. QUIGG

Attesting Officer

Commissioner of Patents and Trademarks